US007217410B2

(12) United States Patent
Suslick et al.

(10) Patent No.: US 7,217,410 B2
(45) Date of Patent: May 15, 2007

(54) SURFACE MODIFIED PROTEIN MICROPARTICLES

(75) Inventors: Kenneth S. Suslick, Champaign, IL (US); Farah Jean-Jacques Toublan, Urbana, IL (US); Stephen A. Boppart, Champaign, IL (US); Daniel L. Marks, Urbana, IL (US)

(73) Assignee: The Board of Trustees of the Universtiy of Illinois, Urbana, IL (US)

( * ) Notice: Subject to any disclaimer, the term of this patent is extended or adjusted under 35 U.S.C. 154(b) by 283 days.

(21) Appl. No.: 10/463,833

(22) Filed: Jun. 17, 2003

(65) Prior Publication Data

US 2004/0258759 A1 Dec. 23, 2004

(51) Int. Cl.
*A61K 51/00* (2006.01)
*A61M 36/14* (2006.01)

(52) U.S. Cl. .................. 424/1.29; 424/1.11; 424/1.37; 424/1.65

(58) Field of Classification Search ............... 424/1.11, 424/1.29, 1.33, 1.37, 1.65, 9.1, 9.3, 9.4, 9.5, 424/9.6, 9.7, 9.8; 428/402, 402.2
See application file for complete search history.

(56) References Cited

U.S. PATENT DOCUMENTS

| | | | |
|---|---|---|---|
| 4,522,811 | A | 6/1985 | Eppstein et al. |
| 5,294,369 | A * | 3/1994 | Shigekawa et al. ............ 516/97 |
| 5,362,478 | A | 11/1994 | Desai et al. |
| 5,439,686 | A | 8/1995 | Desai et al. |
| 5,498,421 | A | 3/1996 | Grinstaff et al. |
| 5,505,932 | A | 4/1996 | Grinstaff et al. |
| 5,508,021 | A | 4/1996 | Grinstaff et al. |
| 5,512,268 | A | 4/1996 | Grinstaff et al. |
| 5,560,933 | A | 10/1996 | Soon-Shiong et al. |
| 5,635,207 | A * | 6/1997 | Grinstaff et al. ............ 424/450 |
| 5,639,473 | A | 6/1997 | Grinstaff et al. |
| 5,648,506 | A | 7/1997 | Desai et al. |
| 5,650,156 | A | 7/1997 | Grinstaff et al. |
| 5,665,382 | A | 9/1997 | Grinstaff et al. |
| 5,665,383 | A | 9/1997 | Grinstaff et al. |
| 5,914,806 | A | 6/1999 | Gordon II et al. |
| 5,930,026 | A | 7/1999 | Jacobson et al. |
| 5,972,493 | A | 10/1999 | Iwasaki et al. |
| 6,068,600 | A | 5/2000 | Johnson et al. |
| 6,156,292 | A | 12/2000 | Quay |
| 6,231,834 | B1 | 5/2001 | Unger et al. |
| 6,246,892 | B1 | 6/2001 | Chance |
| 6,246,901 | B1 | 6/2001 | Benaron |
| 6,249,271 | B1 | 6/2001 | Albert et al. |
| 6,262,706 | B1 | 7/2001 | Albert et al. |
| 6,262,833 | B1 | 7/2001 | Loxley et al. |
| 6,264,917 | B1 | 7/2001 | Klaveness et al. |
| 6,264,918 | B1 | 7/2001 | Johnson et al. |
| 6,280,704 | B1 | 8/2001 | Schutt et al. |
| 6,300,932 | B1 | 10/2001 | Albert |
| 6,312,304 | B1 | 11/2001 | Duthaler et al. |
| 6,315,981 | B1 | 11/2001 | Unger |
| 2002/0054912 | A1 | 5/2002 | Kim et al. |
| 2004/0058458 | A1 | 3/2004 | Anker et al. |

OTHER PUBLICATIONS

Ai, H., M. Fang, S. Jones &Y. Lvov, "Electrostatic layer-by-layer nanoassembly on biological microtemplates: platelets," *Biomacromolecules*, 3:560-564, 2002.
Amsden, B., "The production of uniformly sized polymer microspheres," *Pharm. Res.*, 16:1140-1143, 1999.
Amsden, B. & M. Gossen, "An examination of factors affecting the size, distribution, and release characteristics of polymer microbeads made using electrostatics," *J. Control. Release*, 43:183-196, 1997.
Barton, J., J. Hoying, & C. Sullivan, "Use of microbubbles as an optical coherence tomography contrast agent," Contrast Material Research Conference, Sep. 12-17, 1999, Woodstock, VT, in *Academic Radiology* 9 (Supp. 1):S52-S55, 2002.
Boppart, S., B. Bouma, C. Pitris, J. Southern, M. Brezinski & J. Fujimoto, "In vivo cellular optical coherence tomography imaging," *Nature Med.*, 4:861-865, 1998.
Boppart, S., B. Bouma, C. Pitris, G. Tearney, J. Southern, M. Brezinski & J. Fujimoto, "Intraoperative assessment of microsurgery with three-dimensional optical coherence tomography," *Radiology*, 208:81-86, 1998.
Boppart, S., B. Bouma, C. Pitris, G. Tearney J. Fujimoto & M. Brezinski, "Forward-imaging instruments for optical coherence tomography," *Optics Letters*, 22:1618-1620, 1997.
Boppart, S., M. Brezinski, B. Bouma, G. Tearney & J. Fujimoto, "Investigation of developing embryonic morphology using optical coherence tomography," *Devel. Biol.*, 177:54-63, 1996.
Boppart, S., M. Brezinski, C. Pitris, & J. Fujimoto, "Optical coherence tomography for neurosurgical imaging of human intracortical melanoma, *Neurosurgery,*" 43:834-841, 1998.
Boppart, S., B. Bouma, M. Brezinski, G. Tearney & J. Fujimoto, "Imaging developing neural morphology using optical coherence tomography," *J. Neurosci. Meth.*, 70:65-72, 1996.
Boppart, S., G. Tearney, B. Bouma, J. Southern, M. Brezinski & J. Fujimoto, Noninvasive assessment of the developing *Xenopus* cardiovascular system using optical coherence tomography, *Proc. Natl. Acad. Sci. USA*, 94:4256-4261, 1997.
Bouma, B., G. Tearney, S. Boppart, M. Hee, M. Brezinski & J. Fujimoto, "High-resolution optical coherence tomographic imaging using a mode-locked $Ti:Al_2O_3$ laser source," *Optics Letters*, 20:1486-1488, 1995.
Bouma, B., G. Tearney, C. Compton & N. Nishioka, "High-resolution imaging of the human esophagus and stomach in vivo using optical coherence tomography," *Gastrointest. Endosc.*, 51:467-474, 2000.
Brezinski, M., G. Tearney, B. Bouma, J. Izatt, M. Hee, E. Swanson, J. Southern & J. Fujimoto "Optical coherence tomography for optical biopsy: properties and demonstration of vascular pathology," *Circulation*, 93:1206-1213, 1996.

(Continued)

*Primary Examiner*—Dameron L. Jones
(74) *Attorney, Agent, or Firm*—Evan Law Group LLC

(57) ABSTRACT

A microparticle contains a cross-linked protein shell, and a surface coating.

29 Claims, 3 Drawing Sheets

OTHER PUBLICATIONS

Bugaj, J., S. Achilefu, R. Dorshow & R. Rajagopalan, "Novel fluorescent contrast agents for optical imaging of in vivo tumors based on a receptor-targeted dye-peptide conjugate platform," *J. Biomed. Opt.*, 6:122-133, 2001.

Burns, R., J. Klaunig, J. Shulok, W. Davis & P. Goldblatt, "Tumor-localizing and photosensitizing properties of hematoporphyrin derivative in hamster buccal pouch carcinoma," *Oral Surg. Oral Med. Oral Pathol.*, 61:368-372, 1986.

Caruso, F., R. Caruso, & H. Möhwald, "Nanoengineering of inorganic and hybrid hollow spheres by colloidal templating," *Science*, 282:1111-1114, 1998.

Chen, Z., T. Milner, S. Srinivas, X. Wang, A. Malekafzali, M. van Gemert & J. Nelson "Noninvasive imaging of in vivo blood flow velocity using optical doppler tomography," *Optics Letters*, 22:1119-1121, 1997.

Christiansen, C., H. Kryvi, P. Sontum & T. Skotland, "Physical and biochemical characterization of Albunex™, a new ultrasound contrast agent consisting of air-filled albumin microspheres suspended in a solution of human albumin," *Biotechnol. Appl. Biochem.*, 19:307-320, 1994.

de Boer, J., T. Milner, M. van Germert, & S. Nelson, "Two-dimensional birefringence imaging in biological tissue by polarization-sensitive optical coherence tomography," *Optics Letters*, 22:934-936, 1997.

Decher, G., "Fuzzy Nanoassemblies: Toward layered polymeric multicomposites," *Science*, 277:1232-1237, 1997.

Desai, N., P. Soon-Shiong, M. Grinstaff, Z. Yao, P. Sandford, K. Suslick & P. Soon-Shiong, "Controlled and targeted drug delivery with biocompatible protein shell microspheres," Abstract from 20$^{th}$ Annual Meeting of Society of Biomolecules, Apr. 4-9, 1994, Boston, MA, *Proc. Soc. Biomaterial*, 20:112, 1994.

Dick, A., G. Adam, J. Tacke, A. Prescher, T. Southon & R. Günther, "Computed tomography of experimental liver abscesses using a new liposomal contrast agent," *Invest. Radiology*, 31:194-203, 1996.

Drexler, W., U. Morgner, F. Käftner, C. Pitris, S. Boppart, X. Li, E. Ippen & J. Fujimoto, "In vivo ultrahigh-resolution optical coherence tomography," *Optics Letters*, 24:1221-1223, 1999.

Freeman, R., K. Grabar, K. Allison, R. Bright, J. Davis, A. Guthrie, M. Hommer, M. Jackson, P. Smith, D. Walter & M. Natan, "Self-assembled metal colloid monolayers: an approach to SERS substrates," *Science*, 267:1629-1632, 1995.

Fu, K., D. Pack, A. Klibanov, & R. Langer, "Visual evidence of acidic environment within degrading poly(lactic-co-glycolic acid) (PLGA) microspheres," *Pharmac. Res.*, 17:100-106, 2000.

Fujimoto, J., M. Brezinski, G. Tearney, S. Boppart, B. Bouma, M. Hee, J. Southern & E. Swanson, "Optical biopsy and imaging using optical coherence tomography," *Nature Medicine*, 1:970-972, 1995.

Gazelle, G., G. Wolf, G. McIntire, E. Bacon, E. Halpern, E. Cooper & J. Toner, "Nanoparticulate computed tomography contrast agents for blood pool and liver-spleen imaging," *Acad. Radiol.*, 1:373-376, 1994.

Geny, B, P. Bischoff, B. Muan, F. Piquard, J. Thiranos, E. Epailly, M. Lambrechs, A. Juelsrud-Vebner, B. Eisenmann & P. Haberey, "Safety of a new transpulmonary echocontrast agent (Albunex®) in repeated echocardiographic studies in patients," *Clin. Cardiol.*, 20:111-115, 1997.

Gram, T., "Drug absorption and distribution," in *Modern Pharmacology with Clinical Applications*. (Craig, CR, R. Stitzel, eds. Little, Brown, & Co., Inc., Boston, MA), pp. 13-24, 1997.

Grinstaff, M. & K. Suslick, "Air-filled proteinaceous microbubbles: synthesis of an echo-contrast agent," *Proc. Natl. Acad. Sci. USA*, 88:7708-7710, 1991.

Hee, M., J. Izatt, E. Swanson, D. Huang, J. Schuman, C. Lin, C. Puliafito & J. Fujimoto, "Optical coherence tomography of the human retina," *Arch. Opthalmol.* 113:325-332, 1995.

Huang, D., E. Swanson, C. Lin, J. Schuman, W. Stinson, W. Chang, M. Hee, T. Flotte, K. Gregory, C. Puliafito & J. Fujimoto, "Optical coherence tomography," *Science*, 254: 1178-1181, 1991.

Jue, R., J. Lambert, L. Pierce & R. Traut, "Addition of sulfhydryl groups to *Escherichia coli* ribosomes by protein modification with 2-iminothiolane (methyl 4-mercaptobutyrimidate)," *Biochemistry*, 17:5399-5406, 1978.

Kim, K., K. Jang & R. Upadhye, "Hollow silica spheres of controlled size and porosity by sol-gel processing," *J. Am. Ceram. Soc.*, 74:1987-1992, 1991.

Kim, N., K. Kim, D. Payne & R. Upadhye, "Fabrication of hollow silica aerogel spheres by a droplet generation method and sol-gel processing" *J. Vac. Sci., Technol. A.*, 7:1181-1184, 1989.

Korbelik, M. & G. Krosl, "Photofrin accumulation in malignant and host cell populations of various tumours," *Br. J. Cancer*, 73:506-513, 1996.

Langer, R, "Drug delivery and targeting," *Nature*, 392:5-10, 1998.

Lasic D. and D. Paphadjopoulos, "Liposomes revisited," *Science*, 267:1275-1276, 1995.

Lee, R. & P. Low, "Delivery of liposomes into cultured KB cells via folate receptor-mediated endocytosis," *J. Biol. Chem.*, 269:3198-3204, 1994.

Leelarasamee, N., S. Howard, C. Malanga & J. Ma, "A method for the preparation of polylactic acid microcapsules of controlled particle size and drug loading," *J. Microencapsul.*, 5:147-157, 1988.

Li, X., S. Boppart, J. Van Dam, R. Mashimo, M. Mutinga, W. Dexler, M. Klein, C. Pitris, M. Krinsky, M. Brezinski & J. Fujimoto, "Optical coherence tomography: advanced technology for the endoscopic imaging of Barrett's Esophagus," *Endoscopy*, 32:921-930, 2000.

Liu, K., M. Grinstaff, J. Jiang, K. Suslick, H. Swartz & W. Wang, "In vivo measurement of oxygen concentration using sonochemically synthesized microspheres," *Biophys. J.*, 67:896-901, 1994.

Lvov, Y., R. Price, B. Gaber & I. Ichinose, "Thin film nanofabrication via layer-by-layer adsorption of tubule halloysite, spherical silica, proteins and polycations," *Colloids Surf. A*, 198-200:375-382, 2002.

Lvov, Y. & R. Price, "Nanoparticle/polyion assemby on microtemplates (lipid tubules and latex spheres)," *Colloids Surf. B*, 23:251-256, 2002.

Mathias, C., S. Wang, R. Lee, D. Waters, P. Low & M. Green, "Tumor-selective radiopharmaceutical targeting via receptor-mediated endocytosis of Gallium-67-deferoxamine-folate," *J. Nucl. Med.*, 37:1003-1008, 1996.

McNamara III, W., Y. Didenko & K. Suslick, "Sonoluminescence temperatures during multibubble cavitation," *Nature*, 401:772-775, 1999.

Möhwald, H., "From Langmuir monolayers to nanocapsules," *Colloids. Surf. A*, 171:25-31, 2000.

Pinkerton, K., J. Gallen, R. Mercer, V. Wong, C. Plopper & B. Tarkington, "Aerosolized fluorescent microspheres detected in the lung using confocal scanning laser microscopy," *Micros. Res. Tech.*, 26:437-443, 1993.

Pitris, C., A. Goodman, S. Boppart, J. Libus, J. Fujimoto & M. Brezinski, "High resolution imaging of gynecological neoplasms using optical coherence tomography," *Obstet. Gynecol.*, 93:135-139, 1999.

Pitris, C., C. Jesser, S. Boppart, D. Stamper, M. Brezinski & J. Fujimoto, "Feasibility of optical coherence tomography for high-resolution imaging of human gastrointestinal tract malignancies," *J. Gastroenterol.*, 35:87-92, 2000.

Profio, A. & D. Doiron, "Transport of light in tissue in photodynamic therapy," *Photochem. Photobiol.*, 46:591-599, 1987.

Puliafito, C., M. Hee, C. Lin, E. Reichel, J. Schuman, J. Dukar, J. Izatt, E. Swanson & J. Fujimoto, "Imaging of macular diseases with optical coherence tomography," *Ophthalmology*, 102:217-229, 1995.

Sansdrap, P. & A. Moës, "Influence of manufacturing parameters on the size characteristics and the release profiles of nifedipine from poly(DL-lactide-co-glycolide) microspheres," *Int. J. Pharm.*, 98:157-164, 1993.

Schmitt, J., A. Knüttel & R. Bonner, "Measurements of optical properties of biological tissues by low-coherence reflectometry," *Appl. Optics*, 32:6032-6042, 1993.

Schmitt, J., A. Knüttel, M. Yadlowsky & M. Eckhaus, "Optical-coherence tomography of a dense tissue: statistics of attenuation and backscattering," *Phys. Med. Biol.,* 39:1705-1720, 1994.

Schmitt, J., M. Yadlowsky & R. Bonner, "Subsurface imaging of living skin with optical coherence microscopy," *Dermatology,* 191:93-98, 1995.

Sergeev, A., V. Gelikonov, G. Gelikonov, F. Feldchtein, R. Kuranov, N. Gladkova, N. Shakhova, L. Snopova, A. Shakhov, I. Kuznetzova, A. Denisendo, V. Pochinko, Y. Chumakov & O. Streltzova, "In vivo endoscopic OCT imaging of precancer and cancer states of human mucosa," *Optics Express,* 1:432-440, 1997.

Shiga, K., N. Muramatsu & T. Kondo, "Preparation of Poly(D,L-lactide) and Copoly(lactide-glycolide) Microspheres of Uniform Size," *J. Pharm. Pharmacol.,* 48:891-895, 1996.

Sivak Jr., M., K. Kobayashi, J. Izatt, A. Rollins, R. Ung-runyawee, A. Chak, R. Wong, G. Isenberg & J. Willis, "High-resolution endoscopic imaging of the GI tract using optical coherence tomography," *Gastrointest. Endosc.,* 51:474-479, 2000.

Su, M., A. Mühler, X. Lao, and O. Nalcioglu, "Tumor characterization with dynamic contrast-enhanced MRI using MR contrast agents of various molecular weights," *Magn. Reson. Med.,* 39:259-269 (1998).

Suslick, K. & E. Flint, "Versatile sonochemical reaction vessels" in *Experimental Organometallic Chemistry: A Practicum in Synthesis and Characterization,* (A. Wayda, Darensburg MY, eds. ACS Symposium Series, Washington, D.C.) 185, 1987.

Suslick K., "Sonochemistry," *Science,* 247: 1439-1445, 1990.

Suslick, K. & M. Grinstaff, "Protein Microencapsulation of Nonaqueous Liquids," *J. Am. Chem. Soc.,* 112:7807-7809, 1990.

Tearney, G., B. Bouma, S. Boppart, B. Golubovic, E. Swanson & J. Fujimoto, Rapid acquisition of in vivo biological images by use of optical coherence tomography, *Optics Letters,* 21:1408-1410, 1996.

Tearney, G., S. Boppart, B. Bouma, M. Brezinski, N. Weissman, J. Southern & J. Fujimoto, "Scanning single-mode fiber optic catheter-endoscope for optical coherence tomography, " *Optics Letters,* 21:543-545, 1996.

Tearney, G., M. Brezinski, S. Boppart, B. Bouma, N. Weissman, J. Southern, E. Swanson & J. Fujimoto, "Catheter-based optical imaging of a human coronary artery," *Circulation,* 94:3013, 1996.

Tearney, G., M. Brezinski, B. Bouma, S. Boppart, C. Pitris, J. Southern & J. Fujimoto, "In vivo endoscopic optical biopsy with optical coherence tomography," *Science,* 276:2037-2039, 1997.

Tearney, G., M. Brezinski, J. Southern, B. Bouma, S. Boppart & J. Fujimoto, "Optical Biopsy in Human Gastrointestinal Tissue Using Optical Coherence Tomography," *Am. J. Gastroenterol.,* 92:1800-1804, 1997.

Tearney, G., M. Brezinski, J. Southern, B. Bouma, S. Boppart & J. Fujimoto, "Optical Biopsy in Human Urologic Tissue Using Optical Coherence Tomography," *J. Urol.,* 157:1915-1919, 1997.

Toublan, F., K. Suslick, J. Reynolds, S. Hartleben, S. Sitafalwalla & S. Boppart, "Magnetically-inducible optical contrast agents for optical coherence tomography." Optical Society of America Biomedical Topical Meeting, Apr. 7-10, 2002, Miami, FL.

Turkevich, J., P. Stevenson & J. Hillier, "A study of the nucleation and growth processes in the synthesis of colloidal gold," *Discuss. Faraday Soc.,* 11:55-75, 1951.

van der Laan, B., G. Jansen, G. Kathmann, G. Westerhof, J. Schornagel & G. Hordijk, "In vitro activity of novel antifolates against human squamous carcinoma cell lines of the head and neck with inherent resistance to methotrexate," *Int. J. Cancer,* 51:909-914, 1992.

Violante MR & P.B. Dean. "Improved detectability of VX2 carcinoma in the rabbit liver with contrast enhancement in computed tomography," *Radiology,* 134:237-239 (1980).

Wang, D., A. Rogach & F. Caruso, "Semiconductor quantum dot-labeled microsphere bioconjugates prepared by stepwise self-assembly," *Nano Lett.,* 2:857-861, 2002.

Webb, A., M. Wong, K. Kolbeck, R. Magin, & K. Suslick, "Sonochemically produced fluorocarbon microspheres: a new class of magnetic resonance imaging agent," *J. Mag. Res. Imaging,* 6:675-683, 1996.

Wong, M. & K. Suslick, "Sonochemically produced hemoglobin microbubbles," *Mat. Res. Soc. Symp. Proc.,* 372:89-94, 1995.

Yazdanfar, S., I. Kilkarni & J. Izatt, "High resolution imaging of in vivo cardiac dynamics using color doppler optical coherence tomography," *Optics Express,* 1:424-431, 1997.

F. Toublan, et al., "Magnetically-inducible optical contrast agents for optical coherence tomography", presented at the Optical Society of America Biomedical Topical Meeting, Miami, FL, Apr. 7-10, 2002.

Kolbeck, K.J., "The biomedical applications of protein microspheres"., Ph.D. Doctoral Thesis, Department of Chemistry, University of Illinois, Urbana Champaign, pp. iii-xxi, pp. 1-302, (1999).

Schuman, J.S., et al., "Optical coherence tomography of ocular diseases"., Second Edition, chapters 1 & 2, appendix A & B, Slack Incorporated, Thorofare, NJ, (1995).

* cited by examiner

Negatively Charged Microspheres   Positively Charged Material   Negatively Charged Material A     Figure 3     B

|  | No Field | ↑ Field | ↓ Field |
|---|---|---|---|
| Top View | | | |
| Side View | | | |

US 7,217,410 B2

SURFACE MODIFIED PROTEIN MICROPARTICLES

FEDERALLY SPONSORED RESEARCH OR DEVELOPMENT

The subject matter of this application may in part have been funded by the National Science Foundation (BES-0086696). The government may have certain rights in this invention.

BACKGROUND

Biodegradable microparticles are one of the most studied delivery devices in medicine. Microparticles were developed to circumvent problems concerning the fragility and short in vivo half-lives of protein-based drugs. These compounds differ from traditional small-molecule drugs since oral administration usually results in the destruction of proteins and peptides during digestion.

The medical applications of microencapsulation via liposomes, microspheres, and colloids are expanding rapidly. In general, colloidal formulations may provide alternative pharmacological properties to pharmacological agents. In many cases, a drug with low water solubility is formulated as a colloidal emulsion (with a high concentration of the active agent) to deliver the required dose more efficiently. Emulsions, liposomes, and solid aggregates are frequently formed using detergents, phospholipids, or polymeric materials. Liposomes, the most generally studied medical colloid, consist of phospholipid bilayers held together only by weak, non-covalent hydrophobic interactions. Liposomes, however, can encapsulate only aqueous solutions and only up to concentrations limited by osmolarity. Because such colloids are held together only be weak intermolecular interactions, they generally have limited shelf-lives, and more critically, are prone to changes in aggregation state in vivo.

The emerging practical potential of protein microparticles has been realized recently, however. Albunex® is an FDA-approved, air-filled albumin microparticle produced ultrasonically that is used intravenously as a contrast agent for ultrasound imaging and as an echo-contrast agent for echocardiography [11–13]. These microparticles may also be formed with encapsulated liquid, to form a unique colloidal delivery vehicle. By the choice of protein used for the microparticle shell and the material encapsulated within the microparticle, a multitude of biomedical applications have been developed [12, 14–18]. Some of the applications of microparticles include biocompatible blood substitutes, magnetic resonance imaging and echocardiographic contrast agents, and novel drug delivery systems. These are described in the following U.S. Pat. Nos. 5,362,478; 5,439,686; 5,498,421; 5,505,932; 5,508,021; 5,512,268; 5,560,933; 5,635,207; 5,639,473; 5,650,156; 5,665,382 and 5,665,383.

Ultrasonic irradiation of aqueous protein solutions results in the creation of microparticles having a protein shell. Studies have delineated that the mechanism responsible for microparticle formation is a combination of two acoustic phenomena: emulsification and cavitation. Ultrasonic emulsification creates the microscopic dispersion of the protein solution necessary to form the shape of the proteinaceous microparticle shell. Emulsification alone is insufficient to produce long-lived microparticles. This is attributed to the fact that the interactions between protein subunits that maintain the proteins within the microparticle shell's architecture are not strong enough to overcome entropy-driven dissociation. For example, while emulsions generated by vortex mixing produce microparticles, these particles will disassemble into individually solvated protein components over time.

Ultrasonic irradiation of liquids can also produce cavitation, which is the formation, growth, and implosive collapse of bubbles. The collapse of such bubbles creates transient hot-spots with enormous peak temperatures [9]. Sonolysis of water is known to produce a variety of reactive species, such as $H^+$, $OH^-$, $H_2$, $H_2O_2$, and in the presence of oxygen, $HO_2$ [10]. These species recombine to form water, escape from solution as gas, or undergo further reaction among themselves and with other solution components. Among the various reactions that occurs with sonolysis of protein solutions is the formation of inter-protein crosslinked products. Sonolysis-produced superoxide creates inter-protein disulfide bonds that cross-link the protein components of a microparticle, thereby imparting the requisite stability necessary for maintaining the microparticle shell's architecture over time. Thus, the dispersion of gas or nonaqueous liquid into the protein solution to create a microparticle shell, coupled with chemical cross-linking of the protein at the microparticle interface, results in the formation of long-lived microparticles filled with air or liquid.

SUMMARY

In a first aspect, the present invention is a microparticle, comprising a cross-linked protein shell, and a covalently-attached surface coating.

In a second aspect, the present invention is a microparticle, comprising a cross-linked protein shell, and a surface coating comprising particles.

In a third aspect, the present invention is a method of making a microparticle, comprising coupling polyethylene glycol to a cross-linked protein shell.

In a fourth aspect, the present invention is a method of making a microparticle, comprising mixing a microparticle having a surface charge with a colloid. The colloid comprises the particles, and the particles have a charge opposite the surface charge.

In a fifth aspect, the present invention is a method of making a microparticle, comprising mixing an aqueous solution of a protein with the particles suspended in oil, to form a mixture; and irradiating the mixture with ultrasound to cross-link the protein and form the microparticle.

BRIEF DESCRIPTION OF THE FIGURES

FIGS. 3(a) and (b) are electron micrographs of microparticles having melanin (a) and carbon (b) surface coats;

DETAILED DESCRIPTION

The targeting of drugs to specific tissue types remains a natural, but largely unrealized, goal of medical research. Microparticles are nearly an ideal colloidal carrier system because they have an easily modified surface, and therefore a controllable pharmacokinetic profile, and because they are able to deliver many types of pharmaceuticals, including drugs, x-ray opaque materials, and MRI contrast agents.

The present invention makes use of the discovery that microparticles can be created with modified outer shell protein compositions that possess unique stability characteristics in solution as well as selective affinity properties for surfaces. Particles of differing stability are advantageous to afford timed decomposition of the outer shell of the microparticle that may be important to programmed delivery of its contents in particular contexts. Particles that display selective affinity properties for different surfaces is important to targeted delivery of microparticles to different cell, tissue, or organ types. Further, microparticles that display selective affinity for different biological surfaces have applications in therapy and diagnosis. The combined characteristics of microparticle stability and selectivity are specified largely by the composition of its outer proteinaceous coat layer and surface coating.

The following is presented to aid the practitioner, although other methods, techniques, cells, reagents, and approaches can be used.

The word "microparticle" refers to a particle of crosslinked protein that is either hollow or filled.

Preferably, the microparticles have an average diameter of at least 100 nm, more preferably at least 0.5 microns, even more preferably 0.5–15 microns, most preferably 0.5–5 microns. Preferably, the microparticles have an average diameter of at most 50 microns, more preferably 100 nm to 50 microns. As used herein, the term "diameter" and "average diameter." in the context of microparticles, means number average diameter.

Any protein may be used in the microparticles. The term "protein" includes proteins, peptides, and polypeptides, both natural and synthetic.

Figure 1:
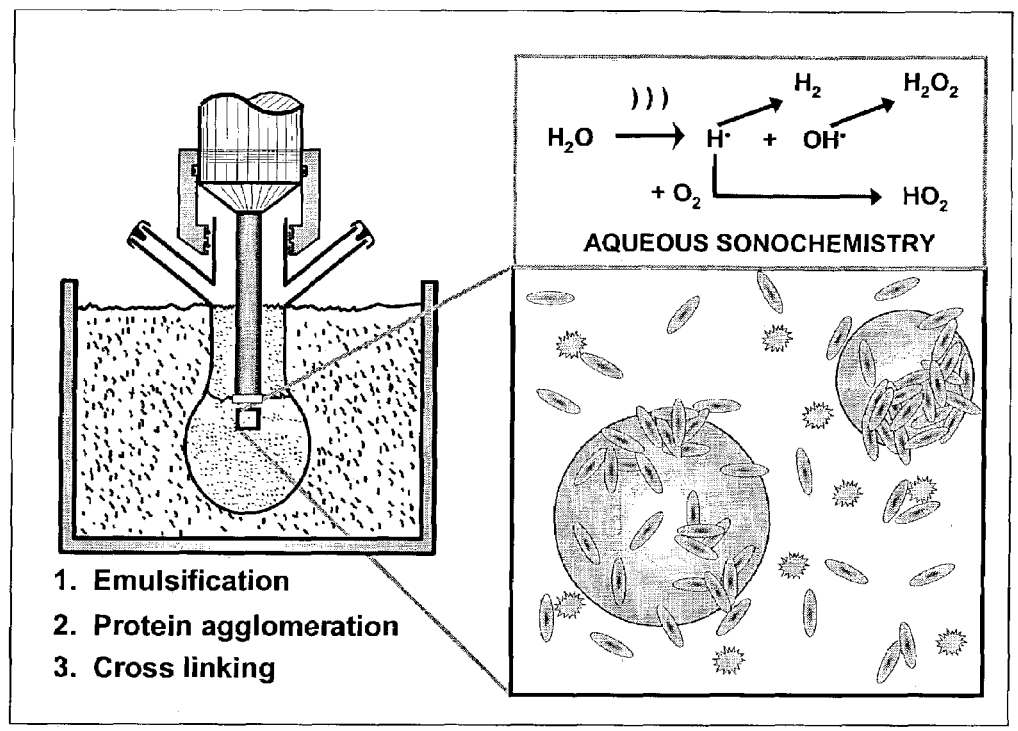
FIG. 1 is an illustration of the process for forming microparticles.

In the fabrication of microparticles, there are three main steps: emulsification, protein agglomeration, and cross-linking. The first two steps are a result of the mixing effect caused by ultrasound. The third step is a result of the sonolysis of water. When expose to high intensity ultrasound (20 kHz), water molecules are split into highly reactive intermediates. Superoxide, which is produced during the sonolysis of water, cross-links the protein molecules. The cross-linking of the protein components in microparticles is done via the oxidation of the cysteine residues to form inter-protein disulfide bounds. The general process is depicted in FIG. 1. Using the particular step-up, a variety of microparticles may be produced.

Sonochemical methods that use high-intensity ultrasound and simple protein solutions may be used to make both air-filled microparticles and liquid and solid-filled microcapsules [5]. Microparticle diameter can be controlled by varying the acoustic power of the ultrasound wave. This sonochemical technique produces micron-sized particles with a cross-linked protein shell and a core which may be selected freely.

Native protein and extensively purified microparticles show very similar spectra. Formation of microparticles does not significantly alter the secondary structure of the protein that makes up the cross-linked shell. For example, microparticles containing pancreatic lipase in the outer shell retain enzyme activity like that of the free enzyme. Thus, microparticle formation using sonolysis is compatible with the maintenance of protein structure and function. This is significant because protein shells containing native cell surface ligands will retain their structural integrity for molecular recognition by cell surface molecules that specifically bind to the ligands.

During the formation of the microparticles, cysteine residues are reacted, forming disulfide bonds that cross-link the protein. If the protein does not contain cysteine residues, the protein may be modified with 2-iminothiolane (Traut's reagent) using the chemical scheme shown below [19].

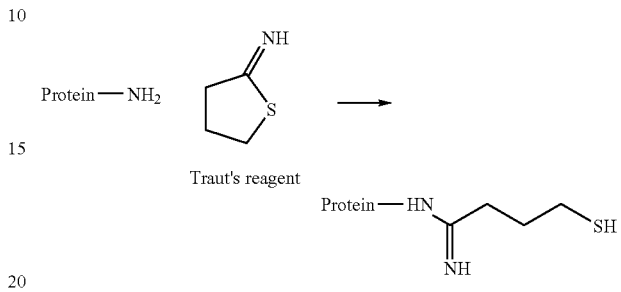

The more thiol groups introduced, the greater the microparticle yield and stability. This is consistent with the fact that cross-linking is done via inter-protein disulfide bond formation. Once modified, any protein can be used for microparticle synthesis. One embodiment describes the modification of myoglobin, a protein naturally devoid of cysteine residues, that renders the protein suitable for fabrication of stable microparticles.

The present invention includes the fabrication of microparticles that possess novel protein shells. Such microparticles may be useful as affinity resins, delivery vehicles to target particular cancer cell types or microbial pathogens like bacteria and viruses, or to serve as dual tropic contrast agents to visualize particular subsets of cell types in vivo. Novel protein shells may be useful to control the overall stability of the microparticle, to direct the types of chemical modifying agents that may be used to apply the surface coat to the microparticle, to direct the specific incorporation of particular constituents into the particle or on its surface or to specify the types of surfaces to which microparticles may bind.

For example, recombinant fusion proteins may be synthesized that contain affinity motifs for particular resin surfaces, such as the $His_6$-amino acid repeat that displays high affinity for metal-chelate resins like Ni-NTA. Microparticle shells containing such fusion proteins can be used to immobilize microparticles to Ni-NTA resins for a variety of purposes, such as for performing under semi-solid phase conditions the surface coat addition chemistry of the types disclosed herein or for partitioning complex mixtures, such as biologically or pharmaceutically active materials from contaminants or toxins.

A surface modified microparticle contains a cross-linked protein shell and a surface coating. The surface coating may be covalently-bonded to the cross-linked protein shell or it may be electrostatically-adhered to the cross-linked protein shell. The phrases "surface coating" and "surface coat" have the same meaning and may be used interchangeably herein.

A surface modified microparticle can be fabricated in many ways. In several of the embodiments, the microparticle having only an unmodified protein shell is initially constructed using sonolysis. Thereafter, the surface of the microparticle may be subjected to modification chemistry to create the surface coat on the particle. In another embodiment, the proteins that form the ultimate shell are initially modified to contain a surface coat on individual proteins.

Thereafter, so-modified proteins are subjected to sonolysis to fabricate the final microparticle that contains a surface coat. The microparticle having modified myoglobin provides only one example of the types of chemical modifications that can be accomplished by this latter embodiment.

The latter embodiment may yield surface coats on both the interior and exterior surfaces of the microparticle shell. This may be advantageous in particular contexts where preservation of the surface coat may serve an important secondary function, such as delivery of a toxin, a pharmaceutically-active compound, or a biologically- or chemically-labile species to the target site of interest. In other contexts, the former embodiment may be advantageous for efficient addition of a surface coat to only the outer surface of the microparticle.

One versatile feature of this invention is that the native structure of the protein is not absolutely critical for microparticle fabrication. As described previously, stable microparticle formation depends only upon the presence of reactive sulfhydryl groups in the protein for the purposes of sonolysis-mediated protein cross-linking. Protein fragments, partially- or fully-denatured proteins in soluble form, and even polypeptides can be used to form the protein shell of the microparticles. In these particular embodiments, the functional utility of the microparticle might be more reliant upon the nature of the surface coat on its outer layer.

The surface of the microparticles can be altered to vary the in vivo pharmacokinetics and biodistribution. Towards this goal, surface coats include, but are not limited to, polyethylene glycol chains (PEG) (to extend the lifetime of the microparticles in the blood pool), membrane receptor ligands (e.g., folate, hemes, steroids, neurotransmitters, piperidine-based sigma receptor ligands), bioactive peptides, and even antibody chains. In these examples, the ligand of interest is covalently-attached to the cross-linked protein shell of the microparticle through side chains of amino acid residues of the protein shell.

The availability of numerous functionalizable side groups in proteins makes it possible to fabricate microparticles with novel surface coats. Only three requirements for surface modification of side group functionality must be met. First, some of the side chains of the amino acids that form the protein must be accessible to solvent to undergo reaction with the modification chemistry. Side chains groups that are buried within the interior of the protein shell or that lie within the protein tertiary structure may not be solvent accessible to the modification chemistry. Second, and related to the first requirement, the target functionality of the side chain must not reside in an environment of secondary or tertiary structure that may sterically hinder the reaction with the modification chemistry. Third, and most importantly, the functionality of the side group must remain chemically reactive following formation of the microparticle. For example, cysteines may not be readily available for modification following sonolysis, as the sulfhydryl groups often participate in disulfide bond formation within the context of the protein shell.

If present, the free sulfhydryl group of an available cysteine may form mixed disulfide derivatives with other thiol-containing compounds, such as other disulfide compounds. Alternatively, cysteine sulfhydryl functionality may serve as a nucleophile to react with a halide-containing compound, such as an alkyl halide or a haloacetamide, or with a maleimide to form a thioether.

Although the chemical reactivity of alcohol hydroxyl groups of threonine, serine, and tyrosine is low in aqueous solution, these groups may be selectively modified, especially if they are reactive groups within enzyme active sites. Certain N-terminal serine or threonine groups that exist in a non-acylated form in proteins may be oxidized with periodate to yield aldehydes, which can be modified with a variety of amine or hydrazine derivatives. Still other alcohol hydroxyl groups can be selectively modified, like the tripeptide sequences of certain peptides wherein serine, threonine or tyrosine residues are separated from a histidine residue by a single amino acid (e.g., Ser-X-His, Thr-X-His and Tyr-X-His), by succinimidyl or sulfosuccinimidyl esters or by N-succinimidyl-3-(4-hydroxy-5-[$^{125}$I]iodophenyl)propionate (Bolton-Hunter reagent).

The alcohol functionality of tyrosine may be selectively modified in several ways. As an indirect method, these groups may be subjected to an initial nitration of the ortho position of its phenol using tetranitromethane, followed by reduction of the o-nitrotyrosine with sodium dithionite ($Na_2S_2O_4$) to form an o-aminotyrosine. The resultant aromatic amine of o-aminotyrosine can react with most amine-reactive reagents. In another approach, the phenol group in tyrosine residues may be converted to salicylaldehyde derivatives, followed by a reaction of the resultant salicylaldehydes with amine or hydrazine derivatives to yield the modified protein surfaces.

The carboxylic groups of aspartate or glutamate may be coupled to hydrazines or amines in aqueous solution using water-soluble carbodiimides such as 1-ethyl-3-(3-dimethylaminopropyl)carbodiimide (EDAC). Including N-hydroxysuccinamide or N-hydroxysulfosuccinimide in the reaction mixture may improve the coupling efficiency of EDAC-mediated protein-carboxylic acid conjugations. To reduce intra- and inter-protein coupling to lysine residues, which is a common side reaction, carbodiimide-mediated coupling may be performed in a concentrated protein solution at a low pH, using a large excess of the nucleophile.

The amine groups of lysine, glutamine, and arginine may form amide linkages following coupling to reactive ester compounds. Alternatively, these amine groups may serve as general nucleophiles with compounds having appropriate leaving group reactive chemistry, such as alkyl halides or maleimides.

Photochemical reagents may represent an alternative strategy for modifying the surfaces of microparticles. Particularly useful for the present invention are multi-functional photoreagents having at least one photoreactive functionality and at least one non-photoreactive chemical functionality. Examples of groups with a photoreactive functionality include aryl azides and benzophenone derivatives. Examples of groups with a non-photoreactive chemical functionality include sulfhydryls, amines, alcohols, esters, carbonyls, carboxylates, and halides. The photoreagent may be coupled to the protein shell of the microparticle using an irradiation source corresponding to the $\lambda_{max}$ of the photoreactive species. The photoreaction may proceed by a radical reaction, wherein the photoreactive species forms a covalent bond with any amino acid residue in the cross-linked protein shell of the microparticle. The photoreactive species may form covalent bonds with tyrosine, phenylalanine, or tryptophan of the cross-linked protein shell, should the wavelength of excitation overlap the respective $\lambda_{max}$ of the photoreactive species and the $\lambda_{max}$ of any of these amino acid residues. Subsequent surface modification on the microparticle may be effected using the secondary chemical functionality attached to the photoreagent.

Modification of microparticles allows for prolonged circulation in the case of polyethylene glycol (PEG) attachment, surface recognition in the case of folate and antibodies attachment, and changes in optical and spectroscopic properties in the case of colloids adhesion. For example, the protein shell of serum albumin microparticles with a n-$C_9F_{20}$ core can be modified. In rats, the measured circulation half-life of non-modified microparticles was approximately 5 minutes, while surface modification with PEG extends this to more than 70 minutes. In this fashion, the surface modification may extend the in vivo lifetime of the microparticle. "Polyethylene glycol" includes polymers of ethylene glycol, and moieties and compounds containing —$(CH_2CH_2O)$— units, preferably with a mass of at least 150 daltons, preferably at least 3,000 daltons.

Polyethylene glycol (PEG) may be covalently attached to amine or hydroxyl groups on the microparticle. The amino moiety of lysine and glutamine resides can be modified to introduce functionality such as the polyethylene glycol (PEG) group. Likewise, the hydroxyl moiety of serine, threonine, and tyrosine may be modified to introduce similar functionality as observed with the amino moiety. The introduction of the PEG group may be done via a coupling reaction with cyanuric chloride, which is reactive with both amino and hydroxyl moieties. The reaction scheme with an amine moiety on the cross-linked protein shell is shown below.

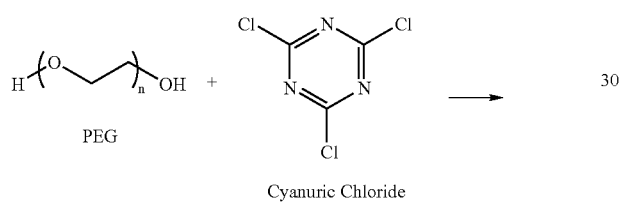

PEG        Cyanuric Chloride

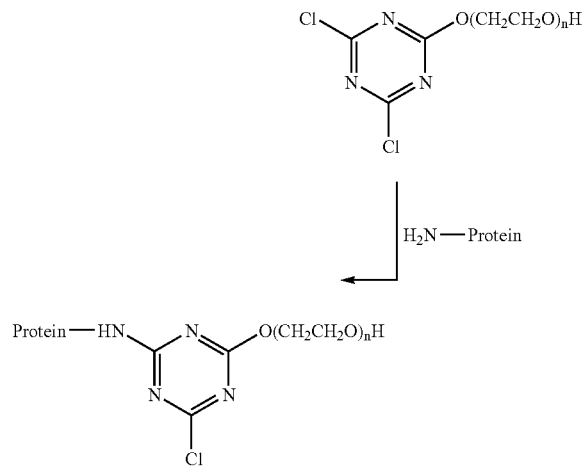

Surface modification using folate is an extension of the PEG surface modification method shown above. The folate in this instance may be activated using N-hydroxysuccinamide in a dicyclohexyl carbodiimide (DCC) coupling reaction. The activated folate then may be coupled to a PEG moiety containing an amino group functionality to form an amide bond between PEG and folate. This process is depicted below. The resultant modified PEG may be attached to the surface of the microparticles in the same manner as depicted above via a cyanuric chloride coupling reaction.

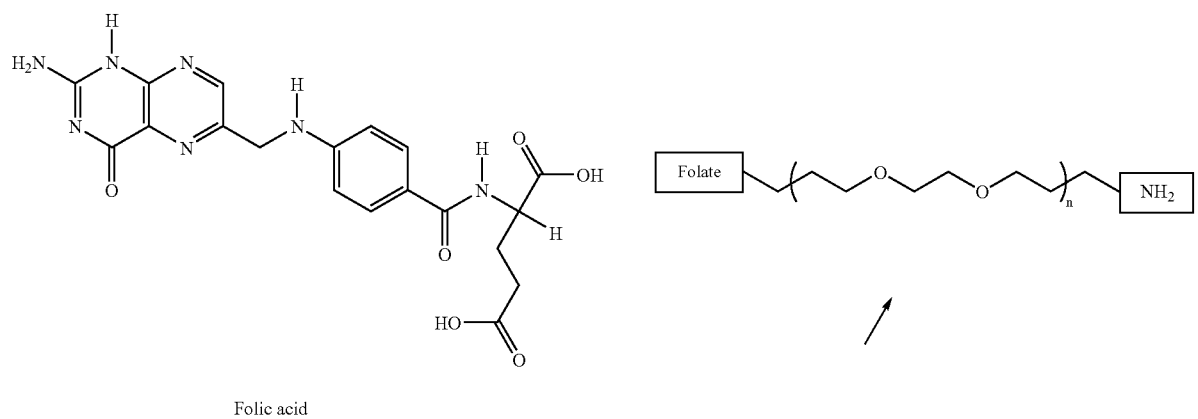

Folic acid

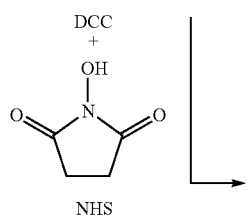

NHS

-continued

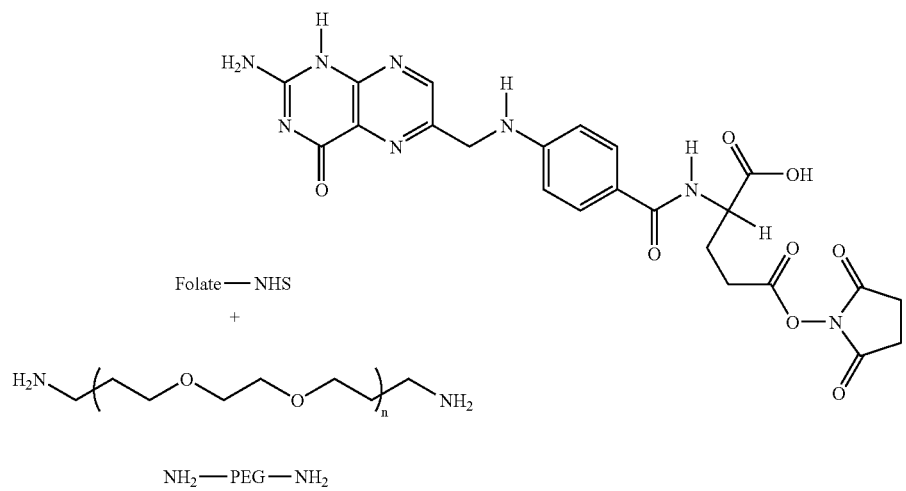

Folate—NHS

+

NH$_2$—PEG—NH$_2$

This example represents one embodiment whereby the surface of microparticles may be modified to contain any ligand using a combination of the preceding chemical reaction schemes. Thus, one may chemically attach PEG to the desired ligand using known coupling chemistry. The PEG-ligand derivative is then coupled to cyanuric chloride and the resultant cyanuric-PEG-ligand compound is reacted with available amines of the protein shell of microparticles to yield the desired surface modifications. Although the preceding reaction schemes may permit mono-substituted PEG derivatives to be attached at each site of modification in the cross-linked protein shell, the presence of three functionally reactive chlorines in cyanuric chloride may allow for more extensive coupling with the PEG derivative. The use of cyanuric chloride may be advantageous in those cases where each surface modification on the cross-linked protein shell may bear a di-substituted PEG derivative. Optionally, one may use any bifunctional protein crosslinking reagent instead of cyanuric chloride and react the resultant PEG-ligand compound with any type of nucleophile present on the microparticle surface.

The conjugation of folate to the microparticle surface allows targeting to folate-binding tumor cells. Ovarian, breast, and human nasopharyngeal tumors all possess a high concentration of folate receptors on their surface [20,21]. Prior work has shown that liposomes modified by folate-PEG conjugates target folate receptor bearing KB tumor cells and exhibit an inhibitory effect on their growth [22]. Specifically, these contrast agents are expected to target induced squamous cell carcinoma with the folate-modified microparticles. Similarly, many oral and upper gastrointestinal tract tumors have a high affinity for various hemes (which greatly assists in the use of hematoporphyrins as photodynamic therapy agents) [23,24]. Microparticles with surface hemes attached may also be used to target induced squamous cell carcinoma.

The modification of the microparticles with immunoglobulins allows targeting of T-cell receptors. This modification may be carried out using monoclonal antibodies that are specific for T-cell receptors. These monoclonal antibodies may be covalently linked to the surface of the microparticles via a dimethylaminopropyl-carbodiimide hydrochloride (EDC) coupling reaction according to the general scheme shown below. In this coupling reaction, the carboxylic acid moiety of a glutamate residue in the protein to be attached to the microparticle (depicted in the scheme as "Glutamate-CO$_2$H") may be activated through reaction with EDC. The monomeric forms of the protein containing EDC-activated carboxylic ester on its surface may be purified and subsequently reacted with an amino moiety from an amino acid in the cross-linked protein shell of the microparticle (depicted in the scheme as "Lysine-NH$_2$"). The lysine amino moiety of the microparticle surface forms a covalent isopeptide bond with a glutamate residue in target antibody protein. Optionally, the order of the reactions may be reversed wherein EDC is initially reacted with carboxylic acid moieties in amino acid residues of the cross-linked protein shell of microparticles, followed by secondary reaction with lysine moieties in amino acid residues of the antibody protein ligand to form the microparticle with an antibody surface coating. In this fashion, the coupling reaction may be used to form a surface coat of any protein that contains available carboxylic acid or amino moieties. Furthermore, carboxylate moieties on the protein my be used for surface modification by reaction with amines, or by esterification.

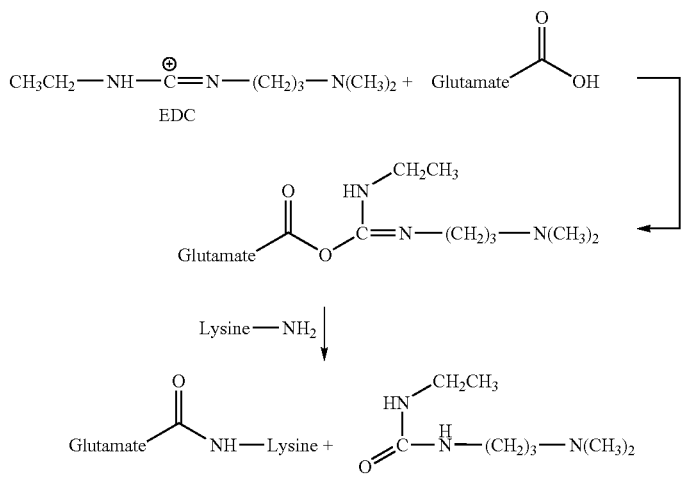

Microparticles, including those containing or lacking a surface coat, may be readily purified from fabrication solutions or recovered following their use in a preferred application. Microparticles are extremely large, as compared to their individual protein constituents. The microparticles may be pelleted by centrifugation, thereby permitting for extensive purification by sequential washing and centrifuging steps. Microparticles containing an immunoglobulin surface coat optionally may be separated from unmodified microparticles by chromatography on a Sepharose-Protein A column. The population of unmodified microparticles would be in the void volume, as they lack the capacity to bind protein A. Those microparticles with an immunoglobulin surface coat would adhere to the Protein A and may be eluted from the resin with mild acid treatment. Still other microparticles with affinity-tagged surface coats may be purified from unmodified microparticles using resins and techniques unique to the structural affinity principle incorporated in the surface coat.

Modifications using aqueous colloidal suspension relies on the surface charge of the microparticles for particle adhesion. This method has been employed in the thin film industry to place charged particles onto a template. The net surface charge on a microparticle may be determined experimentally by isoelectric focusing. The isoelectric point, pI, is defined as the pH at which the microparticle displays zero net charge. To a first approximation, the pI of the individual protein components that make up the cross-linked protein shell of the microparticle reflect the pI of the microparticle. At buffer conditions where the pH may be above pI, the microparticle may display an overall net negative charge. Under such conditions, the microparticle may be fabricated with a surface coating bearing particles with a positive charge. At buffer conditions where the pH may be below pI, the microparticle may display an overall net positive charge. Under such conditions, the microparticle may be fabricated with a surface coating bearing particles with a negative charge. The surface coating in both cases is electrostatically-adhered to the cross-linked protein shell of the microparticle by virtue of the attractive electrostatic interactions between oppositely-charged materials.

Figure 2:
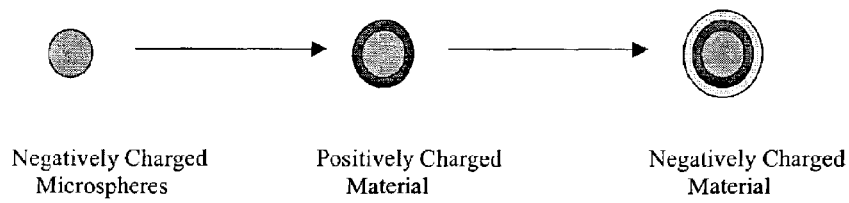
FIG. 2 depicts a method of coating colloidal suspensions onto microparticles.

Microparticle shells bearing an outer colloidal adhesion surface coating of like charge may be fabricated in the following manner. The microparticle are mixed with a primary colloidal particle of opposite charge, resulting in formation of an outer electrostatic-adhesion colloidal layer on the cross-linked protein shell. If the electrostatically-adhered colloidal layer contains sufficient remnant net charge that is identical to the primary colloidal particle, then the resultant microparticle may be mixed with a secondary colloidal particle whose charge is opposite that of the primary colloidal layer to form an additional surface coating. The resultant microparticle may contain as a composite surface coating a sandwich colloidal layer of opposite charge. For example, a microparticle having a negatively charge protein shell is formed and materials with opposite charge characteristics may be adhered onto the surface following a successive, layer-by-layer approach, by simply mixing microparticle with the colloidal material. This method is depicted in FIG. 2.

Other materials may be put on the surface by following the usual microparticle synthesis route but by using a non-colloid suspension of the desired material in the oil phase. Because the oil does not appropriately solvate the suspended particles, upon microparticle formation these particles preferentially attach to the exterior of the protein shell to avoid contact with the oil phase. Examples of these microparticles are the melanin and carbon surface coat containing microparticles. These microparticles are illustrated in FIG. 3.

Examples of material, colloidal and non-colloidal include: ceramics, such as oxides (e.g., titanium oxide, zirconium oxide, aluminum oxide, silica, glass, silicon oxynitride, iron oxide, and mixtures thereof), nitrdies (e.g., titanium nitride, silicon nitride, and mixtures thereof), carbides (e.g., titanium carbide, silicon carbide, tungsten carbide, and mixtures thereof) and silicides (e.g., tungsten silicide, titanium silicide, and mixtures thereof); metals, such as copper, gold, silver, nickel, iron, cobalt, palladium, platinum, zinc, chromium, aluminum, lead, rare earth metals, and mixtures thereof; and semi-conductors, such as silicon, germainium, alloys of silicon and germanium, III-V semiconductors (e.g. gallium arsenide, aluminum phosphide, gallium nitride, and alloys thereof), and II-VI semiconductors (e.g. cadmium selenide, zinc sulfide, and alloys thereof).

Different surface protein modifications are possible that render the resultant microparticles stable under different environmental or physicochemical conditions. Protein shells that are inert to environmental conditions may provide for enhanced storage of the microparticle's internal contents.

Such stability might preserve or otherwise extend the shelf-life of bioactive ingredients of pharmaceutical compounds. The biodegradable component of the protein shell may permit an inert microparticle to release its contents when it is needed during therapy.

Methods of surface protein modification that render resultant microparticles labile under different physicochemical conditions also represent an aspect of the present invention. Depending upon the route of administration, microparticles that possess stability characteristics uniquely suited for the biological environment of action may be fabricated. For example, surface protein modification that are acid-labile may be desirable for administrating pharmaceutically active compounds to treat infections or disorders of the stomach and GI tract. Microparticles that target other tissues or organs might need to preserve their integrity, and modifications that are acid stable may be advantageous for those microparticles that are administered orally. Yet other microparticles may not require an acid labile characteristic if they are administered in other ways, such as by an intravenous pathway.

The most efficient approach to drug therapy is to selectively deliver the drug at the intended site of ultimate effect. One of the objectives of the present invention is a method for surface protein modification that renders the resultant microparticles selective for different surfaces, particularly biological samples. Protein shells of microparticles can be modified to contain ligands that are recognized by cell surface receptors (e.g., hormones, growth factors, cytokines, etc.), integral membrane proteins, or cell-type or neoplasm specific markers. For example, immunoglobulin-modified microparticles may be used to target delivery of drugs to cell types bearing a particular cell surface antigen by virtue of the affinity of the immunoglobulin specific for that antigen. Such modalities are advantageous in medical treatments. As one benefit, a physician may treat tissue-specific illnesses or genetic disorders without wasting drugs, thereby promoting cost-effective medical care. As another benefit, the selectivity of the delivery strategy may minimize unwanted side-effects of the drug on other tissues, reducing patient pain and health care requirements.

One or more materials may be encapsulated in each microparticle. Changes in the inner core allows for versatility of the microparticles in biomedical applications. Table 1 lists some of the types of microparticles that have been synthesized. In addition to the inner core materials in the list, melanin granules, colloidal gold, iron oxide, and fluorophores, all of which have the potential to absorb, scatter, spectrally-modify, or modulate the incident radiation, may be used. Still other examples include liquid crystalline materials, biocompatible liquid crystals in the cholesterol family such as cholesterol oleyl carbonate, fatty alcohol esters of tartaric acid and cholesteryl oligo(L-lactic acids), chiral agents such as helocenes, tartaric acid and esters thereof, other optically active organic compounds, and birefringent materials, which may be used in conjunction with planar or circularly polarized light. Dye and pigments may also be included, such as porphyrins, metalloporphyrins, nile red, rhodamine, and phthalocyanines. Preferably, the microparticle are optically dense, the term "optically dense" means that the microparticles absorbs at least twice as much visible light than an equivalent thickness of water-filled microparticles formed from bovine serum albumin. For X-ray application, preferably the microparticles are X-ray dense; the term "X-ray dense" means that the microparticles absorb at least twice as much $Cu_{K\alpha}$ X-ray radiation, than an equivalent thickness of water-filled microparticles formed from bovine serum albumin.

TABLE 1

| Microparticles | | |
|---|---|---|
| Protein Shells | Inner Cores | Surface Coats |
| Albumin | Air, $O_2$, $N_2$, Ar | PEG |
| Hemoglobin | Vegetable oil | Fluorescein |
| Pepsin | Water | Iron oxide colloid |
| Immunoglobulins | Organic liquids | Immunoglobulins |
| Lipase | Acetoacetate | Folate |
| Peroxidases | Fluorocarbons | Gd complexes |
| Modified Myoglobin | Iodinated agents | Monoclonal Antibodies |
| Gold Labeled Albumin | Gd complexes | Gold nanoparticles |
| | Iron Oxide | Silica nanoparticles |
| | | Melanin |
| | | Carbon |

The present invention also includes a method of diagnosing a disease using surface modified microparticles with an imaging system. Microparticles can be fabricated to contain a contrast agent as an interior core and with an appropriate surface modification on the protein shell to permit selective targeting to the desired target tissue. When such microparticles are administered to a patient, the contrast agent may be concentrated at the site of the tissue to be detected. The biological location of the contrast agent is determined by using an imaging method, such as ultrasound, computed tomography, magnetic resonance imaging, optical microscopy, or optical coherence tomography. These and other methods for use of microparticles as contrast agents are described in U.S. patent application Ser. No. 10/463,835, entitled "OPTICAL CONTRAST AGENTS FOR OPTICALLY MODIFYING INCIDENT RADIATION," to Stephen A. Boppart et al., filed the same day as this application, the contents which are hereby incorporated by reference.

Two or more different materials may be encapsulated in each microparticle to provide high or low contrast under different conditions, such as in an applied alternating field. As an example, one or more of the encapsulated material is either charged (for electrically-modulated agents) or magnetic (for magnetically-modulated agents). These agents may be responsible for either low or high contrast. The second type of material to be encapsulated is intended to provide the opposite contrast of the first such as titanium oxide, or may be a bulk material such as oil, or both. Examples of charged agents include Reichardt's dye (RD; a solvatochromic agent) and 1-ethyl-4-methoxycarbonyl) pyridinium iodide (PYI). Examples of magnetic agents include iron particles, iron oxide, ferrox cube A, alnico 8, cunife, cunico, iron particles coated titanium oxide (formed by sputtering the iron particles with titanium oxide), and cobalt particles coated with gold (formed by plating of gold onto cobalt particles).

Sonochemically-generated contrast agents containing any combination of shell and encapsulated material (as shown in Table 1) may be used to increase local contrast within biological and non-biological specimens and samples. Contrast agents can be delivered to the area of interest by a number of techniques including syringe injection interstitially, intravenously, intramuscularity, subdermally, intraperitoneally, and intrathecally. Other techniques include oral, rectal and topical administration. The surface modifications to the agents enable them to localize to target tissues or cells by means include receptor-mediated adhesion, antigen-antibody localization, or phagocytosis (engulfing) or endocytosis (uptake) by target cells.

Once contrast agents have reached their target tissue or cell, they may remain localized and provide contrast either passively or actively. Passive contrast agents may absorb, scatter, or spectrally-modify the incident radiation. Active contrast agents have their contrast modulated by alternating, externally-applied electric or magnetic fields.

Figure 4:
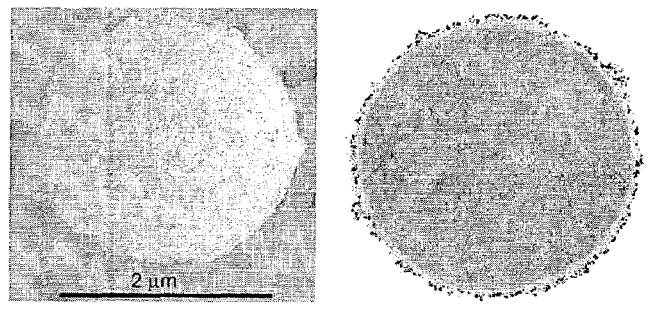
FIG. 4 is a schematic of magnetically- or electrically switchable contrast agents.

Electromagnetic radiation is directed toward the specimen, sample or part of a patient containing the contrast agent. Following interaction with the contrast agent, the affected radiation is detected, typically in either the transmitted (forward) or reflected (backward) directions relative to the direction of the incident radiation. This detected radiation carries information about the specimen, sample or patient, as well as the presence of the contrast agent. This information can be measured and displayed numerically, graphically, or in the form of an image. For active contrast agents that have their contrast modulated by an external field, an alternating electric or magnetic field is applied, inducing an alternating contrast within the agents (FIG. 4). The contrast will modulate at the same frequency as the applied field. Detection with a lock-in amplifier (locked in at the same frequency as the applied field) is used to enhance the sensitivity of the contrast agents. The detection of a signal at the lock-in frequency may be amplified, compared to other signals, thereby enhancing the sensitivity of the detection scheme.

The lifetime of the contrast agents in living specimens is likely to range from minutes to days, depending on the stability of the agent, the ability of the agent to localize and attach to specific tissue or cells, and the ability of the body to breakdown or clear the agent. Studies of similar agents used in ultrasound and MRI indicate that the agents are cleared rapidly within hours and excretion occurs via both the renal (kidneys) and hepatic (liver) systems. Because of the expected rapid clearance of the agents, side-effects are expected to be minimal.

The microparticles may be prepared as pharmaceutical compositions. Such compositions typically include microparticles and a pharmaceutically acceptable carrier. A "pharmaceutically acceptable carrier" includes any and all solvents, dispersion media, coatings, antibacterial and antifungal agents, isotonic and absorption delaying agents, etc., compatible with pharmaceutical administration [26]. Preferred examples of such carriers or diluents include but are not limited to, water, saline, finger's solutions, dextrose solution, and 5% human serum albumin. Liposomes and non-aqueous vehicles such as fixed oils may also be used. Except when a conventional media or agent is incompatible with an active compound, use of these compositions is contemplated. Supplementary active compounds can also be incorporated into the compositions.

A pharmaceutical composition is formulated to be compatible with the intended route of administration, including intravenous, intradermal, subcutaneous, oral, inhalation, transdermal (i.e., topical), transmucosal, and rectal administration. Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

Injection provides a direct and facile route of administration, especially for tissue that is below the skin. Pharmaceutical compositions suitable for injection include sterile aqueous solutions or dispersions and sterile powders for the extemporaneous preparation of sterile injectable solutions or dispersion. For intravenous administration, suitable carriers include physiological saline, bacteriostatic water, CREMOPHOR EL (BASF, Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. The carrier can be a solvent or dispersion medium containing, for example, water, ethanol, polyol (such as glycerol, propylene glycol, and liquid polyethylene glycol), and suitable mixtures. Proper fluidity can be maintained, for example, by using a coating such as lecithin, by maintaining the required particle size in the case of dispersion and by using surfactants. Various antibacterial and antifungal agents, such as parabens, chlorobutanol, phenol, ascorbic acid, and thimerosal, can control microorganism contamination. Isotonic agents, such as sugars, polyalcohols such as manitol, sorbitol, and sodium chloride can be included in the composition.

Sterile injectable solutions or dispersions can be prepared by incorporating microparticles in an appropriate solvent with one or a combination of ingredients, followed by sterilization. Sterile powders for the preparation of sterile injectable solutions methods of preparation include vacuum drying and freeze-drying that yield a powder and any desired ingredient from a sterile solutions.

Oral compositions generally include an inert diluent or an edible carrier. For the purpose of oral administration, the microparticles can be incorporated with excipients and used in the form of tablets, troches, or capsules. Oral compositions can also be prepared using a fluid carrier for use as a mouthwash, wherein the compound in the fluid carrier is applied orally. Pharmaceutically compatible binding agents, and/or adjuvant materials can be included. Tablets, pills, capsules, troches and the like can contain any of the following ingredients, or compounds of a similar nature; a binder such as microcrystalline cellulose, gum tragacanth or gelatin; an excipient such as starch or lactose, a disintegrating agent such as alginic acid, PRIMOGEL, or corn starch; a lubricant such as magnesium stearate or STEROTES; a glidant such as colloidal silicon dioxide; a sweetening agent such as sucrose or saccharin; or a flavoring agent such as peppermint, methyl salicylate, or orange flavoring.

For administration by inhalation, the compounds are delivered as an aerosol spray from a nebulizer or a pressurized containers that contains a suitable propellant, e.g., a gas such as carbon dioxide.

Systemic administration can also be mucosal or dermal. For mucosal or dermal administration, penetrants that can permeate the target barrier(s) are selected. Mucosal penetrants include, detergents, bile salts, and fusidic acid derivatives. Nasal sprays or suppositories can be used for mucosal administration. For dermal administration, the microparticles are formulated into ointments, salves, gels, or creams. The microparticles can also be prepared in the form of suppositories (e.g., with bases such as cocoa butter and other glycerides) or retention enemas for rectal delivery.

Oral formulations or parenteral compositions in unit dosage form can be created to facilitate administration and dosage uniformity. Unit dosage form refers to physically discrete units suited as single doses for a subject, containing a effective quantity of microparticles in association with a pharmaceutical carrier.

The pharmaceutical compositions can be included in a kit, container, pack, or dispenser together with instructions for administration. When the invention is supplied as a kit, the different components of the composition may be packaged in separate containers and admixed immediately before use. Such packaging of the components separately may permit better long-term storage.

The reagents included in the kits can be supplied in containers of any sort such that the life of the different components are preserved and are not adsorbed or altered by the materials of the container. For example, sealed glass ampules may contain buffer that have been packaged under a neutral non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include bottles that may be fabricated from similar substances as ampules, and envelopes, that may consist of foil-lined interiors, such as aluminum or an alloy. Other containers include test tubes, vials, flasks, bottles, syringes, etc. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, etc.

Kits may also be supplied with instructional materials. Instructions may be printed on paper or other substrate, and/or may be supplied as an electronic-readable medium, such as a floppy disc, CD-ROM, DVD-ROM, Zip disc, videotape, audio tape, etc. Detailed instructions may not be physically associated with the kit; instead, a user may be directed to an internet web site specified by the manufacturer or distributor of the kit, or supplied as electronic mail.

EXAMPLES

Example 1

Sonochemical Synthesis Of Microparticles

The synthesis of proteinaceous microparticles with high intensity ultrasound has been described previously [12,14,17,25]. In brief, 3 ml of 5% w/v BSA aqueous solution was placed in a glass container. The tip of the ultrasonic horn was positioned in the aqueous phase. The sample was irradiated with ultrasound (XL-2020, Heat Systems, Farmingdale, N.Y.) for 3 min at an initial temperature of 50° C. at 20 kHz at 60 W/cm$^2$. This produced an aqueous suspension of proteinaceous microparticles filled with liquid. The microparticles were separated from the remaining protein solution by sequential centrifuging and washing. Yields were highly sensitive to the temperature during irradiation and must be optimized for the specific experimental configuration. Determination of the size distribution of the microparticles was accomplished with a Coulter® Multisizer II.

Example 2

Fabrication Of Microparticles That Contain A Liquid

Two ml of solution of soybean oil and 3 ml of 5% w/v BSA aqueous solution were placed in a glass container. The tip of the ultrasonic horn was positioned at the interface of the soybean oil and aqueous phases. The sample was irradiated with ultrasound (XL-2020, Heat Systems, Farmingdale, N.Y.) for 3 min at an initial temperature of 50° C. at 20 kHz at 60 W/cm$^2$. This produced an aqueous suspension of proteinaceous microparticles filled with soybean oil. The microparticles were separated from the remaining protein solution by sequential centrifuging and washing. Yields were highly sensitive to the temperature during irradiation and must be optimized for the specific experimental configuration. Determination of the size distribution of the microparticles was accomplished with a Coulter® Multisizer II.

Example 3

Fabrication Of Microparticles With Different Adhesion Coats Using Aqueous Colloidal Suspension Layer-by-layer (LBL) self-assembly is a method that relies on interactions between template and substrates for adhesion [26]. These interactions may be electrostatic, receptor-ligand or attractive binding [27–32]. LBL self-assembly has been employed in the thin film industry to put charged particles onto a charged template in a one-dimensional manner.

Figure 5:
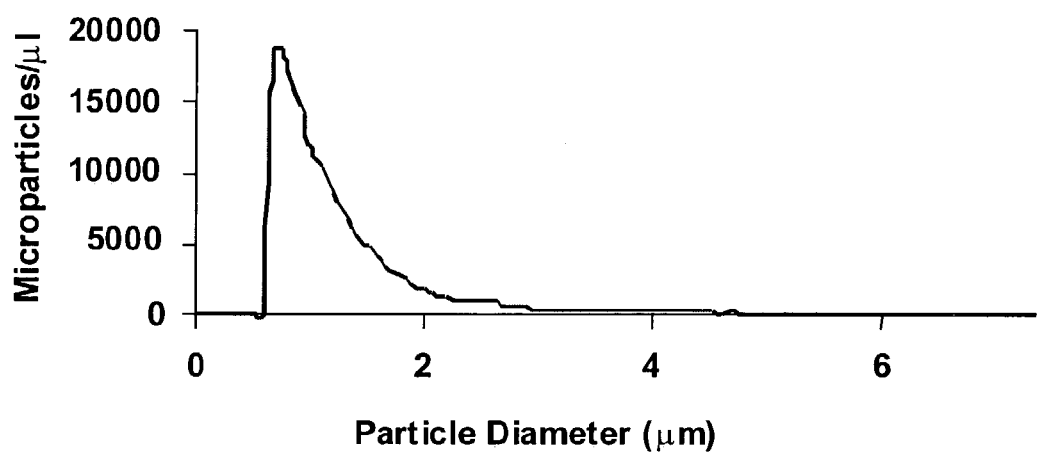
FIG. 5 is an illustration of the size distribution of ultrasonically produced microparticles.

Microparticles provide good templates for electrostatic adhesion as well as metal ligand binding interaction. At pH 7.4, BSA is known to have a net negative charge [33]; hence, it can be assumed that the microparticles retained this negative charge. To this charged surface, positively charged material can be adhered following an electrostatic layer-by-layer approach. The microparticle templates (oil-filled microparticles) were prepared in the usual manner by overlaying an oil phase onto a 5% w/v BSA in the aqueous phase, followed by sonication at 20 kHz for 3 min. The particle size distribution and concentration of these microparticles were obtained using a Coulter® particle counter. A typical size distribution of these microparticles is shown in FIG. 5.

The samples were also examined by electron microscopy to determine the morphology and cleanliness of the surface. To this protein surface both silica colloids and gold colloids were introduced using the adhesion method discussed by Decher [26].

Example 4

Fabrications Of Microparticles With A Silica Coat

Figure 6:
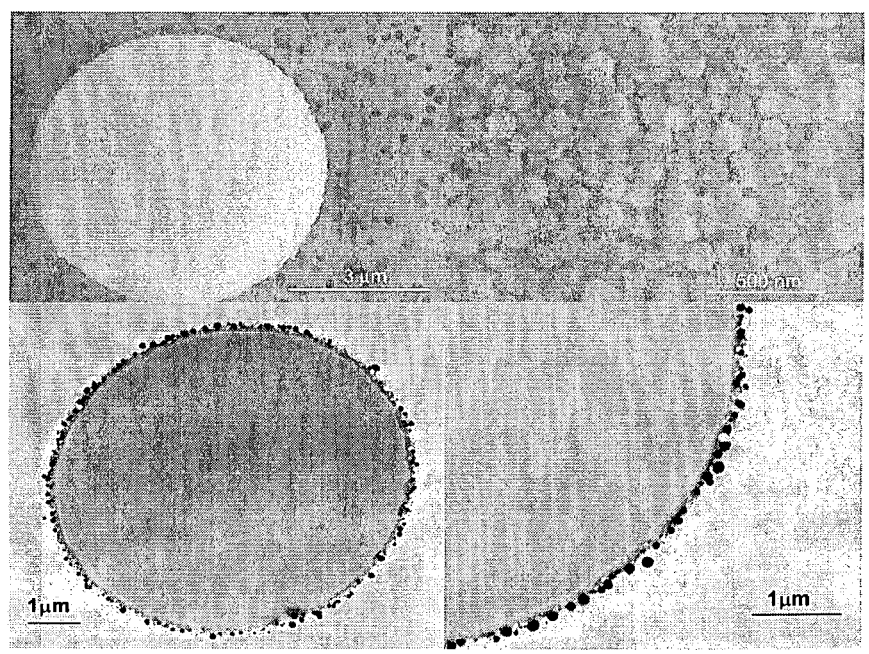
FIG. 6 is electron micrographs of silica-coated microparticles.

The silica beads, which have a net negative surface charge at pH 7, could not be layered directly onto the surface of the microparticles. Positively charged polyion, polydimethyl diallyl ammonium chloride (PDDA), was first adhered in order to reverse the surface charge [32]. This was done by adding an equal volume of microparticle solution to a 1 mg/ml solution of PDDA. The adhesion was allowed to take place with gentle shaking for 25 min. Subsequently, the microparticles were collected following three round of centrifugal washing. Once this polymer addition was completed, a positive surface was presented for silica adhesion. This adhesion was done in a similar manner as the previous adhesion round. An equal amount of a 1% silica colloidal solution was added to the polymer coated microparticle solution. Adhesion was done with gentle shaking for 25 min followed by three centrifugal washes to remove any excess silica. Addition of two subsequent layers of a positively charged polymer (PDDA) and of a negatively charged polymer polystyrene sulfonate trapped the silica colloid and gave rise to a negatively charged surface. FIG. 6 illustrates electron micrographs of the resultant microparticles.

Example 5

Fabrication Of Microparticles With A Gold Coat

BSA is also known to interact very strongly with gold nanoparticles via its amine and thiol residues [34]. Because of the presence of thiol and amine groups, the microparticle can be used as a template for the adhesion of gold nanoparticles. Addition of positive polymer layer was not performed for adhesion of the gold colloid unto the surface of the microparticle. The gold colloid can adsorb directly onto the protein shell via interaction with thiol and amine groups [34]. The red colloidal gold solution used in this synthesis was prepared via the reduction of chloroauric acid in the presence of sodium citrate [35]. The milky white solution of oil-filled microparticle generated from sonication was poured into a equal amount of the red colloidal gold solution. The mixture was shaken gently for 25 min and allowed to phase separate. Following phase separation, the supernatant took on a reddish color; an indication that the gold particles had been transferred to the microparticles. These microparticles were centrifuge-washed twice and still retained their reddish color.

Example 6

Fabrication Of Surface Modified Microparticles Using Non-Colloidal Suspensions In Vegetable Oil Various materials (carbon, melanin, non-colloidal gold) may be put on the surface of the protein microparticles by following the usual microparticle synthesis route and by using a non-colloidal suspension of the desired material in the oil phase. FIG. 3 illustrates examples of microparticles bearing melanin and carbon surface coats.

To obtain the suspensions, bulk material (purchases from Fisher) may be sonicated in vegetable oil for 30 min. Since the vegetable oil do not appropriately solvate the suspended particles, these particles are confined to the exterior of the protein shell to avoid contact with the oil phase during microparticle formation. This behavior is observed during the attempted encapsulation of a non-colloidal suspension of iron oxide [36].

Example 7

Fabrication Of Microparticles With A Pancreatic Lipase Coat

Pancreatic lipase was dissolved in a 2 ml solution of ethanol-water (35% [v/v]) at a concentration of 2 mg/ml. Two ml of vegetable oil was added to the lipase solution. The tip of an inverted ultrasonic horn is positioned in the aqueous phase. The sample was irradiated with ultrasound (XL-2020, Heat Systems, Farmingdale, N.Y.) for 3 min at an initial temperature of 30° C. at 20 kHz at ~100 W/cm$^2$. This produced an aqueous suspension of proteinaceous microparticles having a lipase coat and an aqueous liquid core. The microparticles were separated from the remaining protein solution by sequential centrifuging and washing. The resultant microparticles retained the lipase activity of soluble native pancreatic lipase.

REFERENCES

1. Leelarasamee N, Howard S A, Malanga C J, Ma J K H. A method for the preparation of polyactic acid microspheres of controlled particle size and drug loading. J. Microencapsul. 5:147–57, 1988.

2. Sansdrap P, Moes A J. Influence of manufacturing parameters on the size characterisitcs and the release profiles of nifedipine from poly(DL-lactide-co-glycolide) microspheres. Int. J. Pharm. 98:157–64, 1993.

3. Shiga K, Muramatsu N, Kondo T. Preparation of poly(DL-lactide) and copoly(lactide-glycolide) microspheres of uniform size. J. Pharm. Pharmacol. 48: 891–95, 1996.

4. Amsden, B G, Goosen, M. An examination of the factors affecting the size, distribution, and release characteristics of polymer microbeads made using electrostatics. J. Control. Release 43: 183–96, 1997.

5. Amsden B. The production of uniformly sized polymer microspheres. Pharm. Res. 16:1140–43, 1999.

6. Kim N K, Kim K, Payne D A, Upadhye R S. Fabrication of hollow silica aerogel spheres by a droplet generation method and sol-gel processing. J. Vac. Sci., Technol. A. 7:1181–84, 1989.

7. Kim K, Jang N Y, Upadhye R S. Hollow silica spheres of controlled size and porosity by sol-gel processing. J. Am. Ceram. Soc. 74:1987–92, 1991.

8. Kim K, Pack D W, Berkland C. Microparticles. U.S. patent application Ser. No. 09/931,640, filed Aug. 15, 2001 and published May 9, 2002.

9. McNamara III W B, Didenko Y, Suslick K S. Sonoluminescence temperatures during multibubble cavitation. Nature 401:772–775, 1999.

10. Suslick K S. Sonochemistry. Science 247:1439, 1990.

11. Christiansen C, Kryvi H, Sontum P C, Skotland T. Physical and biochemical characterization of Albunex, a new ultrasound contrast agent consisting of air-filled albumin microparticles suspended in a solution of human albumin. Biotechnol. Appl. Biochem. 19:307–320, 1994.

12. Grinstaff M W, Suslick K S. Proteinaceous microbubbles: synthesis of an echo contrast agent. Proc. Natl. Acad. Sci. USA 88:7708–7710, 1991.

13. Geny B, Bischoff P, Muan B, Piquard F, Thiranos J C, Epailly E, Lambrechs M, Juelsrud-Vebner A, Eisenmann B, Haberey P. Safety of a new transpulmonary echocontrast agent (Albunex) in repeated echocardiographic studies in patients. Clin. Cardiol. 20:111–115, 1997.

14. Suslick K S, Grinstaff M W, Protein microencapsulation of nonaqueous liquids. J. Am. Chem. Soc. 112: 7807–7809, 1990.

15. Webb A G, Wong M, Kolbeck K J, Magin R L, Wilmes L J, Suslick K S. Sonochemically produced fluorocarbon microparticles: a new class of MRI contrast agents. J. Mag. Res. Imaging. 6:675–683, 1996.

16. Desai N P, Soon-Shiong P, Grinstaff M W, Yao Z, Sandford P A, Suslick K S. Controlled and targeted drug delivery with biocompatible protein shell microparticles. Proc. Soc. Biomaterial 20:112, 1994.

17. Liu K J, Grinstaff M W, Jiang J, Suslick K S, Swartz H M, Wang W. In vivo measurement of oxygen concentration using sonochemically synthesized microparticles. Biophys. J. 67:896–901, 1994.

18. Wong M, Suslick K S. Sonochemically produced hemoglobin microbubbles. *Hollow and Solid Spheres and Microparticles* Wilcox D L, et. al., eds. Matl. Res. Soc., Pittsburgh, pp 89–94, 1995.

19. Jue R, Lambert J M, Pierce L R, Traut R R. Addition of sulfhydryl groups to *Escherichia coli* ribosomes by protein modification with 2-iminothiolane. Biochemistry 17:5399–5406 (1978).

20. van der Laan B F, Jansen G, Kathmann G A, Westerhof G R, Schornagel J H, Hordijk G J. In vitro activity of novel antifolates against human squamos carcinoma cell lines of the head and neck with inherent resistance to methotrexate. Int. J. Cancer 30:909–914, 1992.

21. Mathias C J, Wang S, Lee R J, Waters D J, Low P S, Green M A. Tumor-selective radiopharmaceutical targeting via receptor-mediated endocytosis of gallium-67-deferoxamine-folate. J. Nucl. Med. 37:1003–1008, 1996.

22. Lee R J, Low P S. Delivery of liposomes into cultured KB cells via folate receptor-mediated endocytosis. J. Biol. Chem. 269:3198–3204, 1994.

23. Burns R A, Klaunig J E, Shulok J R, Davis W J, Goldblatt P J. Tumor-localizing and photosensitizing properties of hematoporphyrin derivative in hamster buccal pouch carcinoma. Oral Surg. Oral Med. Oral Pathol. 61:368–372, 1986.

24. Korbelik M, Krosi G. Photofrin accumulation in malignant and host cell populations of various tumors. Br. J. Cancer 73:506–513, 1996.

25. Suslick B S, Flint E B. Experimental Organometallic Chemistry: A Practicum in Synthesis and Characterization. Wayda A, Darensburg M Y, eds. ACS Symposium Series, Washington, D.C. 185, 1987

26. Decher, G. Science, 277, 1232–1237, 1997.

27. Lvov, Y, Price, R, Grabver, B, Ichinose, I. Colloids Surf. A 198–200, 375–382, 2002.

28. Lvov Y M, Price R R, Colloids Surf. B 23:251–256, 2002.

29. Wang D, Rogach L A, Caruso F. Nano Lett. 2:857–861, 2002.

30. Caruso F, Caruso R A, Mohwald H. Nanoengineering of inorganic and hybrid hollow spheres by colloidal templating. Science 282:1111–1114, 1998.

31. Ai H, Fang M, Jones S A, Lvov Y M. Electrostatic layer-by-layer nanoassembly on biological microtemplates: platelets. Biomacromolecules 3:560–564, 2002.

32. Mohwald H. Colloids Surf. A 171, 25–31, 2000.

33. Peters T. All about albumin: Biochemistry, Genetics, and Medical Applications, Academic Press, New York, 1996.

34. Freeman R G, Grabar K C, Allison K J, Bright R M, Davis J A, Guthrie A P, Hommer M B, Jackson M A, Smith P C, Walter D G, Natan M J. Science 267:1629–1631, 1995.

35. Turkevich J, Stevenson P C, Hillier J. Discuss. Faraday Soc. 11:55–75. 1951

36. Kolbeck, K J, Suslick, K S. University of Illinois: Urbana-Champaign, 1999.

The invention claimed is:

1. A microparticle, comprising:
   a cross-linked protein shell, and
   a covalently-attached surface coating.

2. The microparticle of claim 1, wherein the protein shell contains at least one moiety selected from the group consisting of amine moieties, hydroxyl moieties, carboxylate moieties and sulfhydryl moieties.

3. The microparticle of claim 1, wherein the surface coating comprises polyethylene glycol.

4. The microparticle of claim 3, wherein the surface coating further comprises a ligand for a cell-surface receptor.

5. The microparticle of claim 4, wherein the ligand is folate.

6. The microparticle of claim 3, wherein the surface coating further comprises a second protein.

7. The microparticle of claim 1, wherein the surface coating comprises a second protein.

8. The microparticle of claim 6, wherein the second protein is an antibody.

9. The microparticle of claim 7, wherein the second protein is an antibody.

10. The microparticle of claim 1, wherein the cross-linked protein shell comprises cross-linked albumin.

11. The microparticle of claim 3, wherein the cross-linked protein shell comprises cross-linked albumin.

12. A microparticle, comprising a cross-linked protein shell, and a surface coating comprising particles.

13. The microparticle of claim 12, wherein the cross-linked protein shell comprises cross-linked albumin.

14. The microparticle of claim 12, wherein the particles are colloidal particles selected from the group consisting of ceramics, metals and semiconductors.

15. The microparticle of claim 12, wherein the particles are selected from the group consisting of melanin, carbon, gold, and silica.

16. The microparticle of claim 1, further comprising a core comprising a pharmaceutically active compound.

17. The microparticle of claim 1, further comprising a core comprising a member selected from the group consisting of Gd complexes, melanin, colloidal gold, iron oxide, titanium dioxide, and fluorocarbons.

18. The microparticle of claim 12, further comprising a core comprising a pharmaceutically active compound.

19. The microparticle of claim 12, further comprising a core comprising a member selected from the group consisting of Gd complexes, melanin, colloidal gold, iron oxide, titanium dioxide, and fluorcarbons.

20. The microparticle of claim 1, further comprising a core comprising a liquid crystalline material.

21. The microparticle of claim 12, further comprising a core comprising a liquid crystalline material.

22. The microparticle of claim 1, wherein the cross-linked protein shell comprises at least one cross-linked protein, the protein selected from the group consisting of hemoglobin, pepsin, immunoglobulin, lipase, peroxidase and myoglobin.

23. The microparticle of claim 12, wherein the cross-linked protein shell comprises at least one cross-linked protein, the protein selected from the group consisting of hemoglobin, pepsin, immunoglobulin, lipase, peroxidase and myoglobin.

24. The microparticle of claim 12, wherein the cross-linked protein shell encapsulates a core.

25. A microparticle, comprising:
   a core, and a shell encapsulating the core, and
   a surface coating on the shell, wherein the shell comprises proteins that are cross-linked together, and the surface coating comprises particles.

26. The microparticle of claim 25, wherein the proteins comprises at least one member selected from the group consisting of albumin, hemoglobin, pepsin, immunoglobin, lipase, peroxidase, and myoglobin.

27. The microparticle of claim 25, further comprising at least one moiety selected from the group consisting of amine moieties, hydroxyl moieties, carboxylate moieties and sulfhydryl moieties.

28. The microparticle of claim 25, wherein the proteins comprise a chemical modification.

29. The microparticle of claim 28, wherein the chemical modification comprises a carbodiimide.

* * * * *

UNITED STATES PATENT AND TRADEMARK OFFICE
CERTIFICATE OF CORRECTION

PATENT NO.       : 7,217,410 B2
APPLICATION NO.  : 10/463833
DATED            : May 15, 2007
INVENTOR(S)      : Kenneth S. Suslick et al.

It is certified that error appears in the above-identified patent and that said Letters Patent is hereby corrected as shown below:

On the Title Page under item 56 Other Publications

Line 1, please insert a space between "&" and "Y".
Line 33, please insert a quotation mark before "Noninvasive".
Line 34, please insert a quotation mark after "tomography".
Line 41, please put "in vivo" in italics.

Page 2 under item 56 Other Publications

Col. 1, line 2, please put "in vivo" in italics.
Col. 1, line 13, please put "in vivo" in italics.
Col. 1, line 37, please put "in vivo" in italics.

Page 3 under item 56 Other Publications

Col. 1, line 9, please put "in vivo" in italics.
Col. 1, line 31, please insert a quotation mark before "Rapid".
Col. 1, line 31, please put "in vivo" in italics.
Col. 1, line 32, please insert a quotation mark after "tomography".
Col. 1, line 41, please put "in vivo" in italics.
Col. 2, line 12, please put "in vivo" in italics.
Col. 2, lines 28 and 29, please put "in vivo" in italics.

Signed and Sealed this

Twenty-seventh Day of November, 2007

JON W. DUDAS
*Director of the United States Patent and Trademark Office*